United States Patent [19]

Arias Alvarez et al.

[11] 4,400,397

[45] Aug. 23, 1983

[54] ANTITHROMBOTIC TREATMENT WITH QUATERNARY AMMONIUM SULFITES AND BISULFITES

[75] Inventors: Jose A. Arias Alvarez, Carpatos, Mexico; Ralph B. Thompson, Oak Brook, Ill.

[73] Assignee: T & R Chemicals, Inc., Clint, Tex.

[21] Appl. No.: 337,121

[22] Filed: Jan. 5, 1982

Related U.S. Application Data

[63] Continuation-in-part of Ser. No. 271,848, Jun. 16, 1981, abandoned, which is a continuation-in-part of Ser. No. 218,414, Dec. 22, 1980, abandoned, which is a continuation-in-part of Ser. No. 164,303, Jun. 30, 1980, abandoned.

[51] Int. Cl.³ .................... A61K 31/14; A61K 31/095
[52] U.S. Cl. .................................... 424/329; 424/325; 424/335
[58] Field of Search .................... 424/162, 248.5, 267, 424/315, 325, 329, 335

[56] References Cited

U.S. PATENT DOCUMENTS 2,367,302   1/1945   Moore .
3,836,639   9/1974   Teler .................................. 424/101
3,906,109   9/1975   Roehm ................................ 424/325

OTHER PUBLICATIONS

Chao, Thrombos. Haemostas (Stuttg) vol. 35, 1976 pp. 717–736.
Shulman, Chem. Abs., vol. 47, 1953 p. 9386.
Gunnison, Fd. Cosmet. Toxicol. vol. 19, 1981 pp. 667–682.
Elias, Abstract of Thromb. Diath Haemorrh, vol. 18 (3–4), 1967 pp. 499–509.
Torda, Abs. of Anaesth. Intens. Care, 1, 293, (1973).
Bourbon, Abs. of J. Eur. Toxicol., vol. 4, No. 3 pp. 205–207 (1971).
Chem. Abs., 9th Coll. Index p. 37336CS & vol. 82, Ab No. 107247f (1975).
Kikugawa J. Pharm. Sci., vol. 61, 1972 pp. 1904–1907.
Rost, "Comparative Invst. of The Pharmacol. Effects of Organically Bonded Sulfurous Acids and of Neutral Sodium Sulfite" in Arb. A. D. Kaiserlichen Gesundheitsamte, vol. 21, 1904 p. 312.

*Primary Examiner*—Anna P. Fagelson
*Attorney, Agent, or Firm*—Cushman, Darby & Cushman

[57] ABSTRACT

Certain quaternary ammonium sulfites and bisulfites display anticoagulant and antithrombotic activity.

17 Claims, No Drawings

ANTITHROMBOTIC TREATMENT WITH QUATERNARY AMMONIUM SULFITES AND BISULFITES

CROSS-RELATED TO RELATED APPLICATIONS

This application is a continuation in part of our U.S. patent application U.S. Ser. No. 271,848 filed June 16, 1981, now abandoned which is completely incorporated herein by reference which in turn is a continuation in part of U.S. Ser. No. 218,414 filed Dec. 22, 1980 now abandoned which is completely incorporated herein by reference which in turn is a continuation in part of my earlier filed U.S. patent application Ser. No. 164,303, filed June 30, 1980, now abandoned, which is likewise completely incorporated hereinto by reference.

BACKGROUND OF THE INVENTION

Inorganic salts of sulfurous acid have heretofore been discovered by one of us (Jose Antonio Arias Alvarez) to have anticoagulant and antithrombotic properties; see U.S. Ser. No. 227,382, filed Jan. 22, 1981 and Ser. No. 271,850 filed June 16, 1981, and now abandoned in favor or copending application Ser. No. 337,176 filed Jan. 5, 1982.

Anticoagulants and antithrombotics are a group of compounds with diversified pharmacologic actions used in a variety of chemical thrombotic disorders. Thrombotic disorders are generally divided into venous thromboses and arterial occlusive disorders. Venous thrombosis of the lower extremities is important because it can cause pulmonary embolism which may be fatal. Heparin and warfarin are commonly used in clinical medicine for prevention and treatment of deep venous thrombosis and pulmonary emboli. Their pharmacological actions are in the inhibition of blood coagulation activity (i.e., heparin) or of synthesis of coagulation factors (i.e., warfarin). Platelets play an important part in arterial thrombosis. Drugs that inhibit platelet aggregation are generally regarded as being potentially useful for prophylactic therapy of arterial thrombotic disorders, including, for example, stroke, myocardial infarction, and peripheral vascular disease. Despite the availability of many agents which possess anti-platelet aggregating properties, only a few are currently under clinical trails (for example, aspirin, dipyridamole, sulfinpyrazone). None of these exhibit unequivocal efficacy. Compounds with more specific pharmacological action are urgently sought in order to provide better medical care for patients with these serious disorders.

An anti-platelet aggregatory agent is a substance which inhibits platelet aggregation.

An antithrombotic agent is a substance which inhibits formation or development of a thrombus (or thrombosis). For present patent purposes, it will be understood that the term "thrombus" or equivalent includes the subject matter of the term "embolus" unless specifically indicated. In general, an antithrombotic agent may display, in the presence of mammalian blood or appropriately prepared plasma, anticoagulant activity and/or anti-platelet aggregatory activity.

BRIEF SUMMARY OF THE INVENTION

There has now been discovered a class of organic agents, the members of which, when introduced, as by ingestion, injection, absorption, or otherwise introduced into a mammal (including man), produce amelioration of a thrombotic condition in mammals and man when used in an antithrombotically effective amount as taught herein.

The active antithrombotic agents of the present invention are organic quarternary salts of sulfurous acid which display anticoagulant and antithrombotic activity.

One class of antithrombotic agents of the present invention is characterized by the formula:

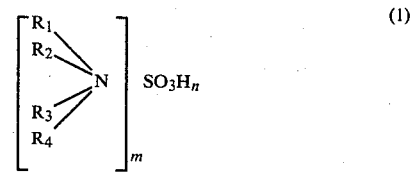

(1)

where:
$R_1$, $R_2$, $R_3$ and $R_4$ are each an independently selected lower alkyl radical
$m+n$ is equal to 2
$n$ is 0 or 1.

Another class of such active agents of the present invention is characterized by the formula:

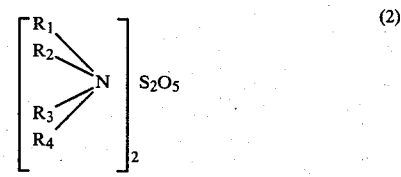

(2)

wherein, in each such formula $R_1$, $R_2$, $R_3$ and $R_4$ have their above specified respective meanings.

Presently preferred such compounds are bisulfite compounds, examples of which include: tetramethyl ammonium bisulfite, tetraethyl ammonium bisulfite, tetrabutyl ammonium bisulfite, trimethyl ethyl ammonium bisulfite, tetramethyl ammonium metabisulfite, and the like. Tetra (lower alkyl) ammonium sulfites are also active agents, however.

The term "lower" as used herein has reference to a radical containing less than 6 carbon atoms each.

Antithrombotic agents of this invention are used in both arterial thrombosis and venal thrombosis. Examples of clinical thrombotic conditions include stroke (as a cerebral vascular thrombosis), myocardial infarction (coronary artery disease), peripheral vascular disease, cardiac valve replacement deep vein thrombosis, pulmonary embolism, and the like.

The mechanisms by which the active agents function is presently unknown; however, an inhibition of platelet aggregation and a prolongation of normal blood coagulation appear to be associated with use thereof in the manner taught by the present invention.

In one aspect, the present invention is directed to the use of certain quaternary bisulfite and sulfite compounds as antithrombotic agents in human medicine.

In another aspect, the present invention is directed to a method for control, and/or prevention of, an embolus or a thrombus in man by oral ingestion and/or injection of a pharmaceutically effective amount of active agent and/or other compound(s) within the scope of active agents of this invention.

In another aspect, the present invention provides symptomatic and objective improvement in a thrombotic (including cardiovascular) disease condition, such as, for example, an abnormal coagulation, or an intravascular thrombosis, in man. By the term "symptomatic improvement", as used herein, reference is had to an improvement in a patient's subjective symptoms (e.g., as reported by the patient). By the term "objective improvement", as used herein, reference is had to a measurable and objective change in a patient's condition.

Naturally, an active antithrombic agent of this invention is used, if at all in a mammal, at a pharmaceutically effective dose rate—that is, at a dose rate which is below the level of toxicity or of production of undesired side effects. Because of biological complexities, the complete biological effects of the active agents of this invention are not now known.

Other and further aspects, objects purposes, advantages, aims, utilities, features and the like will be apparent to those skilled in the art from a reading of the present specification.

DETAILED DESCRIPTION

More particularly, this invention concerns a process for treating a human or other mammal wherein there is introduced, orally, by absorption, and/or by injection into such mammal a pharmaceutically effective amount of a quaternary bisulfite or sulfite active agent of this invention as an antithrombotic.

Sulfite and/or bisulfite anions do not normally occur in human tissues or blood, so far as is now known.

In medicine, for example, arterial thrombosis is diagnosable by clinical manifestations, by arterialgraphy, and recently, by an indium 111 platelet labeling technique (see, for example, the article entitled "Differential Effects of Two Doses of Aspirin on Platelet-Vessel Wall Interaction In Vivo" by K. K. Wu et al being published in the Journal of Clinical Investigation, August, 1981.

Also, in medicine, for example, a thrombus is detectable from patient conditions symptomatically perceivable by a skilled medical practioner and well known to the art of medicine. Objectively, serveral methods including venography, impedance plethysmography, doppler ultransound and the $I^{125}$-fibrinogen test (see, for example the article by Kakkar "Archives of Surgery", Vol. 104, p. 152 (1972) and Kelton, J. G. et al, Journal of Clinical Investigation Vol. 62, pgs. 892-895, (1978)).

The present invention does not contemplate feeding a normal patient (that is, one not suffering from a thrombotic condition) an active agent of this invention at a phramaceutically effective dosage as indicated herein.

By the term "thrombotic condition" as used herein, reference is had both to:
(a) an existing thrombus (including an embolus); and/or
(b) an incipient thrombus (including an incipient embolus).

An "incipient thrombus" or "incipient thrombotic condition," as such a term is used herein can exist in a patient who has a predisposed condition for development of a thrombotic condition. For examples, diabetes mellitus, hyperlipidemia, and the like are conditions which predispose a patient to arterial thrombosis. On the other hand, surgery, trauma, and bed rest, and the like, for a few examples, predispose a patient to venous thrombosis.

Those skilled in the practice of medicine routinely determine the presence of a thrombotic condition (including an actual thrombus in a patient). Such a condition is determined for the present invention preferably by state of the art techniques. Such determination techniques are known to the prior art and do not at such constitute a part of the present invention.

Preferably, to practice this invention in vivo, one introduces into blood of a patient, such as a human, the equivalent of from about 1 to 100 milligrams per kilogram of mammal body weight (including human) per day, though larger and smaller dose rates may be employed, if desired, within the spirit and scope of this invention. The exact amount or dose in any given case is selected to be sufficient and appropriate for achieving a desired antithrombotic effect.

In general, to initiate practice of the present invention, such an introduction may be commenced at a dosage rate within a range as above indicated as soon as a thrombotic condition (or a thrombus) is found to exist in a patient.

Thus, and for example, in a preferred practice of this invention, as a first step, a determination is made that a patient suffers from a thrombotic condition. Then, one starts orally feeding and/or injecting such patient with at least one active agent of the present invention at an effective dose rate in the range above indicated. Presently, more preferred dose rates are believed to be from about 4 to 50 mg/kg per day. Preferably, at least two or three spaced doses per day are employable, each such dose being conveniently administered around meal time. Any convenient dose arrangement can be employed.

Not uncommonly, it is desirable or necessary to start treatment immediately upon the discovery of a patient's thrombotic condition to avoid damage, injury, or perhaps even death of the patient, as from an embolus. If oral administration is not convenient or rapid enough for a situation, the active agent can be directly introduced by injection into a patient, if desired, such as intravenously, intraperitoneally, intramuscularly, subcutaneously, or the like. Absorption through a membrane, such as a dermal layer, may also be used, as when an active agent is dissolved in an appropriate solvent. When an active agent is so directly introduced, it is preferably dissolved in an aqueous medium wherein the total amount of active agent introduced into such medium is preferably within the range from about 1 to 11 weight percent (based on the total solution weight). Distilled water is presently preferred solvent for such a medium. If desired, conventional (standardized) aqueous media can be used as vehicles for such introduction; for example, standard saline solutions can be used as vehicles.

A present perference is to withdraw samples of blood from a patient undergoing treatment and to measure platelet aggregation. One method is described in the paper by Born, Nature, Vol. 194, pgs. 927-292, (1962).

After administration has started, the dose rate is preferably adjusted to a value which is sufficient to disrupt platelet function and/or coagulation factors and thereby achieve a desired antithrombotic effect.

An active agent of this invention, for example, is characteristically capable of lengthening both PT (prothrombin time) and PTT (blood partial thromboplastin time) in vitro. Dose rate of active agent is presently believed to be directly proportional to resulting effects upon blood factors, such as inhibition of platelet aggregation, or the like. Consequently, under this preferred procedure, use of an active agent at a suitable dose for an individual patient ameliorates that patient's thrombotic condition.

Selected blood parameters of a patient are preferably determined before dosing with active agent is started, as when time permits. Preferably, a dose rate adjustment is accomplishable after administration of an active agent has commenced and is continuing. The amount of adjustment (or incremental change in dosage) is determinable by comparing a patient's measured values (such as the patient's own starting corresponding values, normal species e.g. human, values, or the like). Inhibition of platelet aggregation can be used for measurements. Then, the deviation, if any, from the patient's such measured values is compared to such desired values (the patient's starting values, normal species values, or the like). Then, a change in dose rate may be undertaken to correct for any deviations determined.

For instance, in humans, normal values for platelet aggregation are dependent upon the particular agent used for stimulation. For example, when adenosine diphosphate (ADP) at 3 millimolar concentration is employed, platelet aggregation values fall typically in the range between 50 to 100% of light transmission. Other stimulation agents include collagen, epinepherine, arachidonic acid, and the like.

Also, for instance, in humans, normal PT values are believed to fall in the range from about 11 to 13 seconds while normal PTT values are believed to fall in the range from about 25 to 41 seconds. If PT values and/or PTT values could be measured in a given patient, as for purposes of achieving a desired antithrombotic effectiveness, it is currently estimated that a lengthening of PTT value of from about 1.5 to 2 times a PTT value in such normal range in a given starting patient is appropriate (suitable) for antithrombotic effectiveness. This is equal to a lengthened PTT value for a given patient of from about 45 to 60 seconds. Such an estimate is consistent, for example, with the lengthened PTT values achieved in the human use of heparin, a prior art agent sometimes previously employed as an antithrombotic agent. Similarly, it is currently estimated that a lengthening of PT value of about two times a PT value in such normal range in a given starting patient is appropriate (suitable) for antithrombotic effectiveness, which is equal to a lengthened PT value for a given patient of from about 22 to 26 seconds; such an estimate is consistent, for example with the lengthened PT values achieved in the human use of coumadin (warfarin), a prior art agent sometimes previously employed as an antithrombotic agent. The active agents of the present invention, contrary to such prior art agents, appear to affect in vitro both PT and PTT values in a given patient, surprisingly. The mechanism by which the present active agents work is apparently substantially different from, and not comparable to, the prior art agents. Study and evaluation of the active agents of this invention continues.

Contrary to such prior agents (like heparin and coumadin) the active agents of the present invention appear to affect both blood coagulation factors and platelet aggregation. Conveniently and preferably, measurements of blood factors are carried out periodically, such as every 3 to 7 days, on a patient undergoing treatment under the practice of this invention.

An active agent can be orally consumed in the form of a capsule, a tablet, or the like, or in the form of a solution (e.g. aqueous). Also, an active agent can be injected in the form of an aqueous solution.

A particularly presently preferred antithrombotic field of use is in post operative patient treatment, as when arteries or deep veins may be involved in, or threatened by, a thrombotic condition.

By way of explanation, as those familiar with mammalian anatomy appreciate, the venous system in the lower extremities consists of superficial and deep veins. Because of the manner in which the deep veins interconnect and supply blood to the heart and lungs, a thrombus occurring in the deep veins, but not in the superficial veins, can become the source of a blood clot which is moved through the veins and becomes lodged in the lungs, resulting in a pulmonary enbolus, which can have obvious catastrophic effects (including causing death). Examples of deep veins include the iliac, the femoral, the popliteal, calf vein and the like. The prevention of pulmonary emboli following surgery affecting the deep veins in the lower extremities is a significant medical problem. One solution to this problem is to prevent thrombi from occurring and/or developing in deep veins. To achieve this solution, active agents of this invention appear to be well suited. Thus, in one such mode of this invention, one may achieve a symptomatic or objective improvement of a deep vein thrombotic complication in a patient during postoperative care following surgery by inhibiting thrombus formation (including embolism).

In one preferred mode of using this invention, an aqueous solution of from about 1 to 15 percent by weight of an active agent of this invention, is prepared. Then, such solution is orally consumed by a human or injected at the total (or accumulated) dose rate ranging from about 1.0 to 50 mg per each kg of body weight per day, more preferably in the form of at least two spaced doses per day, and still more preferably in the form of at least three spaced doses per day, such a dose being preferably taken around meal time. Solid or encapsulated active agents may be orally consumed alternatively. Because of the tendency for active agents of this invention to undergo oxidation when in aqueous solution, it is presently common and even preferred in practicing this invention to minimize contact of such active agents with oxygen before use.

Compounds (active agents) of this invention are conveniently prepared by preparing an aqueous solution (preferably using a purified or distilled water) of a corresponding lower alkyl quaternary ammonium hydroxide wherein such compound is present at a specified or calculated concentration, such as 10 weight percent. Then, through this solution is bubbled $SO_2$ gas until the resulting solution increases in weight to an extent sufficient to produce a weight corresponding to the desired sulfite or bisulfite salt. For example, to prepare a product solution which is substantially a bisulfite salt twice as much weight increase is needed compared to the corresponding sulfite salt. If the starting quaternary compound is not fully soluble (or fully in a dissolved form) at the start of the sulfur dioxide gas addition (but is partially only dispersed or suspended in the aqueous phase), it becomes completely dissolved as $SO_2$ addition continues. By an alternative synthetic procedure an ion exchange resin in the sulfite form could be used, if desired. Some of the product solutions made from various starting corresponding quaternary compounds can be, after preparation, subsequently evaporated to dry solid form, such as the tetramethyl ammonium bisulfite; others appear to exist only in solution form.

The water used in such a solution of an active agent is preferably purified (e.g., filtered, deionized, distilled, or the like). After preparation, such a solution is preferably stored in a closed container to reduce oxidation.

Such an aqueous solution can be directly used in accordance with the teachings of this invention, in which even such a solution can be dispensed dropwise, or such a solution can be encapsulated, or the like, and uses as measured dosage units, as desired. For example, an aqueous solution containing 5 weight percent of active agent can be injected into a patient or it can be directly consumed by a patient as drops (e.g., from about 5 to 9 drops per meal for each of the two or three meals eaten by such patient per day depending upon an individual patient's body weight, or the like).

Symptomatic improvement in varicose veins and in hemmorrhoids has been observed when using an active agent.

EMBODIMENTS

The present invention is further illustrated by reference to the following case histories. Those skilled in the art will appreciate that other and further embodiments are obvious and within the spirit and scope of this invention from the teachings of these present examples taken with the accompanying specification.

PREPARATION OF ACTIVE AGENTS

Solution A Preparation

A 10 weight percent aqueous solution of tetramethyl ammonium bisulfite is prepared by bubbling $SO_2$ through a solution of tetramethyl ammonium hydroxide to form the desired aqueous product solution.

Solution B Preparation

Using the procedure of Solution A, a 10 weight percent aqueous solution of tetraethyl ammonium bisulfite is prepared from tetraethyl ammonium hydroxide.

Solution C Preparation

Using the procedure of Solution A, a 10 weight percent aqueous solution of trimethyl ethyl ammonium bisulfite is prepared from trimethyl ethyl ammonium hydroxide.

Solution D Preparation

Using the procedure of Solution A, a 5 weight percent solution of tetrabutyl ammonium bisulfite is prepared from tetrabutyl ammonium hydroxide.

Solution E Preparation

A sample of this tetramethyl ammonium bisulfite (Solution A) is evaporated in a Buchi rotary evaporator under vacuum to dryness. When the water is all removed, an oil bath heated to 130° C. is applied to this flask containing the solid and heating under vacuum is continued for 4 more hours thereby removing water from this bisulfite to produce the metabisulfite from the starting bisulfite.

Solution F Preparation

A 5 weight percent aqueous solution of tetramethyl ammonium sulfite is prepared by bubbling $SO_2$ through a solution of tetramethyl ammonium hydroxide to form the desired aqueous product solution. One half as much $SO_2$ is consumed compared to Solution A preparation.

PRACTICE OF THE INVENTION

The Solution A is found to prolong PT and PTT in a dose related fashion. When added to human or rabbit plasma in vitro, the agent tetramethyl ammonium bisulfite is found to significantly prolong PT and PTT at a concentration of 0.5 mg/ml and the effects are dose related (proportional). The agent is active in inhibiting various coagulation factors, including VII, IX, X, XI, and XII.

References for PT, PTT, and assays in vitro of all the coagulation factors can be found in a standard textbook, entitled "Human Blood Coagulation, Haemostasis and Thrombosis", edited by Rosemary Biggs, published by Blackwell Scientific Publications, Oxford, England (2nd edition), pages 670–705, 1976.

EXAMPLE 2

The procedure of Example 1 is repeated using solution B and similar results are obtained.

EXAMPLE 3

The procedure of Example 1 is repeated using solution C and similar results are obtained.

EXAMPLE 4

Solutions A and F are used according to the procedure of Biggs to determine then effect upon PT and PTT. Data from five replications is shown in Table I below. (The concentration of active agent employed is 0.5 mg/ml in each instance.) Both solutions are effective for lengthening blood coagulation time but the bisulfite is more active.

EXAMPLE 5

Solutions of A and F are used according to the procedure of Biggs to evaluate their effect upon fibrinogen and Factors IX and X.

TABLE I

| EFFECT OF QUATERNARY AMINE DERIVATIVES ON COAGULATION (0.01 Molar Concentration) | | | | | | | | | | | |
|---|---|---|---|---|---|---|---|---|---|---|---|
| EXPERIMENT NO. | | | | | | | | | | | |
| #1 | | #2 | | #3 | | #4 | | #5 | | Mean LSD | |
| $PT^{(1)}$ (Sec) | PTT (Sec) | PT (Sec) | PTT (Sec) | PT (Sec) | PTT (Sec) | PT (Sec) | PTT (Sec) | PT (Sec) | PTT (Sec) | PT (Sec) | PTT (Sec) |
| CONTROL 12.9 | 36.7 | 12.9 | 36.2 | 14.4 | 36.4 | 12.2 | 36.0 | 12.1 | 38.9 | 12.3 ± 0.6 | 38.8 ± 1.2 |
| TETRAMETHYL-AMMONIUM BISULFITE 21.7 | 73.4 | 23.7 | 86.7 | 17.8 | 66.2 | 19.1 | 70.0 | 20.1 | 77.0 | 20.5 ± 2.3 | 74.7 ± 7.8 |
| TETRAMETHYL- 17.5 | 59.0 | 19.2 | 67.3 | 16.1 | 57.9 | 17.4 | 61.8 | 18.2 | 70.0 | 17.7 ± | 63.2 ± |

TABLE I-continued
EFFECT OF QUATERNARY AMINE DERIVATIVES ON COAGULATION
(0.01 Molar Concentration)

| | EXPERIMENT NO. | | | | | | | | | | Mean LSD | |
|---|---|---|---|---|---|---|---|---|---|---|---|---|
| | #1 | | #2 | | #3 | | #4 | | #5 | | | |
| | PT[1] (Sec) | PTT (Sec) | PT (Sec) | PTT (Sec) | PT (Sec) | PTT (Sec) | PT (Sec) | PTT (Sec) | PT (Sec) | PTT (Sec) | PT (Sec) | PTT (Sec) |
| AMMONIUM SULFITE | | | | | | | | | | | 1.1 | 5.3 |

[1]PT = Prothrombin time (which measures the integrity of extrinsic coagulation pathway)
PTT = Partial thromboplastin time (which measures the integrity of intrinsic pathway)

The data resulting as shown in Table II and indicates a strong effect upon Factors IX and X and a relative mild effect upon fibrinogen (Factor I).

EXAMPLE 6

Plasma was centrifuged at 100 r.p.m. (200 g) to prepare a platelet rich plasma. Using adenosine diphosphate (ADP) as a stimulus, rapid aggregation of platelets in the plasma was effected. On the other hand, when such plasma is first treated with (a) tetramethyl ammonium sulfite, (b) tetramethyl ammonium bisulfite, and then (c) tetrabutyl ammonium bisulfite, it is found that platelet aggregation in each instance is inhibited, indicating that each of these compounds is a potent inhibitor of platelet aggregation.

EXAMPLE 7

To demonstrate that it is not the quaternary ammonium group which is affecting blood factors, two tests are run evaluating the effect of tetramethyl ammonium bromide and tetra butyl ammonium bromide (Biggs) in vitro on PT and PTT using human plasma. The data shown in Table III indicates that these compounds have little to no effect on PT and PTT when compared to the effect demonstrated by the corresponding bisulfites.

EXAMPLE 8

A rabbit (body weight about 2.3 kg) is continuously infused with aqueous tetrabutyl ammonium bisulfite solution at the rate of 0.400 mg/kg/hr (0.82 gram per hour) for a time of three hours. The rabbit is then injected with fibrinogen labeled with $I^{125}$. After 5 hours, the animal is sacrificed and the radioactive fibrinogen accumulated in the damaged jugular vein is determined. The radioactivity on the contra-lateral (undamaged) jugular vein is also determined to serve as a control.

TABLE II
EFFECT OF QUATERNARY AMINE DERIVATIVES ON SELECTED COAGULATION
(0.01 Molar Concentration)
Factors: Fibrinogen, Factor IX and Factor X

| | Fibrinogen (%)[1] | Factor IX (%)[2] | Factor X (%)[3] |
|---|---|---|---|
| CONTROL | 205 | 50 | 100 |
| TETRAMETHYL-AMMONIUM BISULFITE | 170 | 12.5 | 10 |
| TETRAMETHYL-AMMONIUM SULFITE | 175 | 20 | 25 |

[1]Values shown represent mean of 2 experiments
[2]Value of a single experiment
[3]Mean of 3 experiments

TABLE III
EFFECT OF TETRA ALKYL AMMONIUM BROMIDES
0.5 mg/ml

| | PT (sec) | PTT (sec) |
|---|---|---|
| Tetramethyl Ammonium Bromide | 12.5 | 38.5 |
| Tetrabutyl Ammonium Bromide | 12.4 | 38.3 |
| Control | 12.3 | 38.1 |
| Tetramethyl Ammonium Bisulfite | 21.7 | |
| Control | 12.9 | |

Concurrently another rabbit experienced the same procedure but received only a sodium chloride solution as control. The rabbit from the normal saline solution had approximately 7 times the as much radioactivity as its counterpart infused with tetrabutyl ammonium bisulfite. It is concluded that tetrabutyl ammonium bisulfite shows a definite positive effect of decreasing thrombus formation in the jugular vein.

The same procedure using tetramethyl ammonium bisulfite produced death of the rabbit.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth in the hereto-appended claims.

We claim:

1. A method for treating a thrombotic condition in a mammal comprising administering to said mammal an antithrombotically effective amount of at least one agent characterized by the formulas:

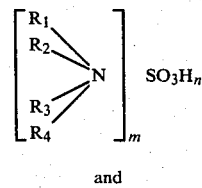

and

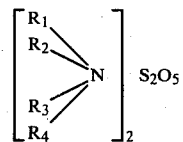

wherein: $R_1$, $R_2$, $R_3$, $R_4$ are each an independently selected lower alkyl radical m and n are integers whose combined sum is equal to 2, and m is 0 or 1.

2. A method for treating a thrombotic condition comprising the step of orally feeding to a patient having a thrombotic condition from about 1 to 100 mg per kg of body weight per day in at least two spaced doses at least one agent having the formulas:

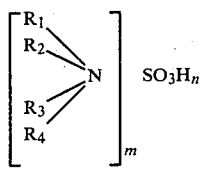

wherein: $R_1$, $R_2$, $R_3$ and $R_4$ are each an independently selected lower alkyl radical, m and n are integers whose combined sum is equal to 2, and n is 0 or 1.

3. The method of claim 2 wherein after said feeding has started, said dose rate is adjusted to a value which is sufficient to cause a desired degree of change in at least one coagulation factor of such patient's blood.

4. The method of claim 3 wherein said agent is tetrabutyl ammonium bisulfite.

5. The method of claim 1 wherein said agent is in the form of an aqueous solution.

6. The method of claim 2 wherein said agent is in the form of an aqueous solution.

7. The method of claim 5 wherein said agent is in the form of an aqueous solution.

8. The method of claim 5 wherein said tetrabutyl ammonium bisulfite is orally fed in dose form selected from the group consisting of capsules and tablets.

9. The method of claim 2 wherein said agent is orally fed to a patient at a dose rate of from about 20 to 50 mg per kg of body weight per day in at least two spaced doses.

10. The method of claim 1 wherein said thrombotic condition is demonstrated by the presence of an existing thrombus in such mammal.

11. The method of claim 1 wherein said thrombotic condition is demonstrated by the existence of an incipient thrombotic condition in such patient.

12. The method of claim 1 wherein said agent is selected from the groups consisting of tetramethyl ammonium bisulfite, tetraethyl ammonium bisulfite, tetrabutyl ammonium bisulfite, trimethyl ethyl ammonium bisulfite, and tetramethyl ammonium metabisulfite.

13. A method for treating a thrombotic condition comprising the steps of injecting into a patient having a thrombotic condition at a dose rate of from about 1 to 100 mg per kg of body weight per day in at least two spaced doses at least one agent having the formulas:

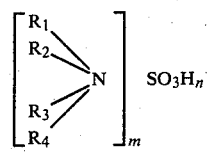

and

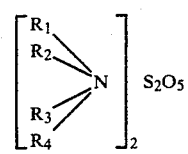

where: $R_1$, $R_2$, $R_3$ and $R_4$ are each an independently selected lower alkyl radical, m and n are integers whose combined sum is equal to 2, and n is 0 or 1.

14. The method of claim 13 wherein after said injecting has started said dose rate is adjusted to a value which is sufficient to cause a desired degree of change in at least one coagulation factor of such patient's blood.

15. The method of claim 14 wherein said adjusting is periodically performed.

16. A method for preventing thrombosis of deep veins following surgery in a human patient comprising the step of treating said human patient post-operatively with an antithrombotically effective amount of at least one agent having the formula:

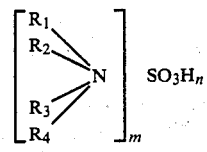

and

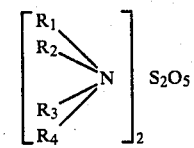

where: $R_1$, $R_2$, $R_3$ and $R_4$ are each an independently selected lower alkyl radical, m and n are integers whose combined sum is equal to 2, and n is 0 or 1.

17. A method of prolonging both the prothrombin time (PT) and partial thromboplastin time (PTT) of the blood or blood plasma of a mammal in need of such therapy, said method comprising administering to said mammal an anticoagulantly effective amount of the agent of claim 1 and continuing said administration until the prothrombin time (PT) and thromboplastin time (PTT) are both prolonged as compared with PT and PTT values of the mammal's blood or blood plasma measured prior to initiating said therapy.

* * * * *